(12) United States Patent
Pies et al.

(10) Patent No.: US 7,399,890 B2
(45) Date of Patent: Jul. 15, 2008

(54) METHOD FOR THE HYDRODEHALOGENATION OF HALOGENATED META-CRESOLS

(75) Inventors: Michael Pies, Duisburg (DE); Klaus Schönauer, Ratingen (DE); Volker Hassmann, Krefeld (DE); Hermann Uhr, Leverkusen (DE)

(73) Assignee: Lanxess Deutschland GmbH, Leverkusen (DE)

( * ) Notice: Subject to any disclaimer, the term of this patent is extended or adjusted under 35 U.S.C. 154(b) by 0 days.

(21) Appl. No.: 10/583,019

(22) PCT Filed: Dec. 7, 2004

(86) PCT No.: PCT/EP2004/013877

§ 371 (c)(1),
(2), (4) Date: Jun. 15, 2006

(87) PCT Pub. No.: WO2005/063663

PCT Pub. Date: Jul. 14, 2005

(65) Prior Publication Data

US 2007/0149829 A1      Jun. 28, 2007

(30) Foreign Application Priority Data

Dec. 19, 2003 (DE) ................. 103 59 794

(51) Int. Cl.
*C07C 39/24* (2006.01)
*C07C 37/00* (2006.01)

(52) U.S. Cl. .................. 568/774; 568/779; 568/797

(58) Field of Classification Search ............ None
See application file for complete search history.

(56) References Cited

U.S. PATENT DOCUMENTS 2,765,335 A  10/1956  Brown et al. ............ 260/621
4,480,140 A  10/1984  Leston ..................... 568/784

FOREIGN PATENT DOCUMENTS

DE       2512509        9/1976

OTHER PUBLICATIONS

Pandey, Paras N., et al.; "Palladium-Catalyzed Hydrodehalogenation of Haloaromatic Compounds," *Synthesis*; 1982, pp. 876-878.

*Primary Examiner*—Sikarl A Witherspoon
(74) *Attorney, Agent, or Firm*—Nicanor A. Kohncke

(57) ABSTRACT

The present process serves for the hydrodehalogenation of halogenated meta-cresols of the formula (I)

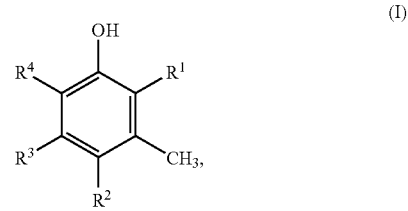

in which the $R^1$ to $R^4$ radicals are each as defined in the description, and is characterized in that halogenated meta-cresols of the formula (I) are contacted with a catalyst which has been prepared by applying one or more salts of palladium and/or platinum and optionally copper salts to an aluminum oxide or titanium oxide support material, together with hydrogen, at temperatures between 100 and 250° C.

10 Claims, No Drawings

METHOD FOR THE HYDRODEHALOGENATION OF HALOGENATED META-CRESOLS

The present invention relates to a process for hydrodehalogenating halogenated meta-cresols by the action of hydrogen in the presence of a catalyst.

In the halogenation of meta-cresol, halogenation products which are of no interest even in industrial and economic terms are frequently obtained owing to non-100% stage and isomer selectivity. For instance, in the preparation of para-chloro-meta-cresol by reaction of meta-cresol with sulfuryl chloride, not only the desired product but also considerable amounts (approx. 15%) of undesired by-products, for example 2-chloro-meta-cresol and 6-chloro-meta-cresol, are formed. Currently, it is customary to remove the undesired bi-products in the industrial preparation of para-chloro-meta-cresol and to incinerate them. Hence, a not inconsiderable fraction of precious starting material is lost in the form of undesired bi-products. There is therefore a need for a process which enables the by-products to be recycled back into the preparation process.

It has been found that, surprisingly, halogenated meta-cresols can be hydrodehalogenated by the action of hydrogen in the presence of specific catalysts without there being any side reactions on the OH or the CH3 group of the aromatic.

The present invention provides a process for hydrodehalogenating halogenated meta-cresols of the formula (I)

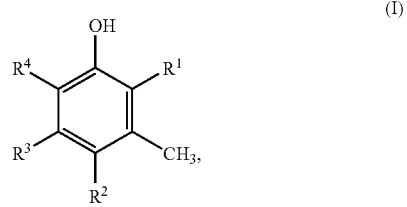

(I)

in which the $R^1$ to $R^4$ radicals are each independently hydrogen or halogen, but at least one of these radicals is halogen, characterized in that halogenated meta-cresols of the formula (I) are contacted with a catalyst which has been prepared by applying one or more salts of palladium and/or platinum and optionally a copper salt to an aluminum oxide or titanium oxide support material, together with hydrogen, at temperatures between 100 and 250° C.

When $R^1$ to $R^4$ in formula (I) represent halogen, it may, for example, be chlorine, bromine or iodine. It is preferably chlorine. Useful starting materials in the process according to the invention are in particular 2-chloro-m-cresol, 6-chloro-m-cresol and the dichlorinated 2,4- and 4,6-dichloro-m-cresols. Preference is given to using mixtures of different halogenated meta-cresols of the formula (I) as are obtained in the preparation of chloro-m-cresol. The process according to the invention preferably serves for the hydrodechlorination of incorrectly chlorinated m-cresols which can be removed by distillation in the workup process of the para-chloro-m-cresol production. Owing to the different boiling points, the monochlorinated 2- and 6-chloro cresols can first be removed by distillation as low boilers. In a further distillation, or in the next step of a batch distillation, the dichlorinated cresols of para-chloro-m-cresol are then likewise distilled off as low boilers before 4-chloro-m-cresol.

Preferred temperatures for the process according to the invention are those in the range from 150 to 250° C.

Hydrogen may be used in customary qualities in the process according to the invention. For example, from 0.5 to 50 mol of hydrogen can be used per mole of halogen in the halogenated meta-cresol (I) used. This amount is preferably from 1 to 30 mol.

It is also possible to use the hydrogen in a mixture with an inert gas, for example nitrogen. The hydrogen content of such mixtures may, for example, be from 10 to 50% by volume. When hydrogen/inert gas mixtures are used, generally at least 1 mol of hydrogen is used per mole of halogen in the halogenated m-cresol of the formula (I) used.

The catalyst is generally prepared by applying palladium and/or platinum salts and optionally copper salts to aluminum oxide or titanium dioxide support material. The salts may, for example, be $PdCl_2$, $PtCl_2$, $PtCl_4$, $CuCl$ or $CuCl_2$. The support materials are customary, preferably particulate $Al_2O_3$ or $TiO_2$ types as are customary for the preparation of supported catalysts. The particles may have different three-dimensional shapes, and are preferably of spherical shape. Preference is given to catalysts which have been prepared from palladium salts and optionally copper salts and support materials with a mean particle size of from 1 to 6 mm and a BET surface area of more than 150 $m^2/g$.

The salts can be applied to the support materials by customary methods, for example by impregnating a solution of the salts and drying or calcinating. For example, from 0.5 to 100 g, preferably from 1 to 50 g of salts per liter may have been applied to the catalysts.

The salts applied to the support material may optionally be reduced before or during the inventive hydrodechlorination.

For example, from 0.5 to 5 mol of halogenated meta-cresols of the formula (I) per hour per liter of catalyst can be passed over the catalyst. This amount is preferably from 1 to 3 mol per hour and liter of catalyst. It is also possible if appropriate to perform the process according to the invention batchwise, but it is preferably performed continuously.

Preferred pressures for the process according to the invention are those in the range from 1 to 5 bar. The pressure and the reaction temperature are preferably combined in such a way that the halogenated meta-cresols of the formula (I) used are contacted with the catalyst in gaseous form.

The reaction mixture which leaves the reactor can be used, for example, in such a way that it is optionally cooled and sent again to a halogenation reaction, preferably chlorination reaction. When, for example, a mixture which has been removed as an undesired by-product, for example by distillation, from the reaction mixture of a chloro-m-cresol preparation is used in the process according to the invention, a hydrodehalogenation mixture is obtained which consists mainly of m-cresol in the process according to the invention. The reaction mixture can then be used again in the chlorination process directly without further workup.

The process according to the invention permits the hydrodehalogenation of halogenated meta-cresols at industrially advantageous low temperatures with good conversions and selectivities at possibly high gas throughputs and thus readily controllable reaction temperatures. With regard to the prior art outlined at the outset, it is particularly surprising that the formation of cyclohexane derivatives is not observed at all in the process according to the invention.

The examples which follow are intended to illustrate the invention without being interpreted as a restriction.

Catalyst A

This comprises aluminium oxide spheres (mean diameter 3 mm) which contain 0.75% Pd Catalyst B Counter-example: Raney Ni tablets Catalyst C 10 g of Pd/l of NORIT®A carbon extrudate Catalyst D Analogous to catalyst A with additionally 0.25% Cu!

EXAMPLE 1

In a reaction tube of length 1400 mm and an internal diameter of 30 mm, 100 g of catalyst A were introduced between two beds of crushed quartz particles (mean size 3 mm) and heated to 180° C. Subsequently, 30 g of crude mixture and 5 l of hydrogen per hour were passed over the catalyst continuously from above. At the end of the reaction tube, the reaction mixture was cooled in a separator, condensed and collected. The composition of the crude mixture and reaction mixture can be seen from the following table 1.

TABLE 1

| Composition | m-cresol % | p-cresol % | 2-Cl-m-cr. % | 6-Cl-m-cr. % |
|---|---|---|---|---|
| Crude mixture | 7.10 | 0.93 | 59.50 | 32.22 |
| Product | 94.70 | 1.28 | 0.53 | 0.52 |

EXAMPLE 2

The procedure of example 1 was repeated except that catalyst B was now used instead of catalyst A. The experiment was performed over a period of 250 hours, in the course of which the composition of the reaction mixture (see table 2 below) changed virtually insignificantly.

TABLE 2

| Composition | m-cresol % | p-cresol % | 2-Cl-m-cr. % | 6-Cl-m-cr. % |
|---|---|---|---|---|
| Crude mixture | 7.10 | 0.93 | 59.50 | 32.22 |
| Product | 19.16 | 2.60 | 49.49 | 26.33 |

EXAMPLE 3

The procedure of example 1 was repeated, except that catalyst C was used:

Here, distinct deactivation can be seen:

| Composition | m-cresol % | p-cresol % | 2-Cl-m-cr. % | 6-Cl-m-cr. % |
|---|---|---|---|---|
| Crude mixture | 7.10 | 0.93 | 59.50 | 32.22 |
| Product | 80.18 | 3.87 | 4.45 | 9.03 |
| Product after 48 h | 45.54 | 3.65 | 26.64 | 23.20 |

EXAMPLE 4

Example 4 was conducted in the same way as example 1, except with catalyst D and double the amount of substance used per unit time. Up to the end of the experiment (several weeks), no deactivation whatsoever was shown.

| Composition | m-cresol % | p-cresol % | 2-Cl-m-cr. % | 6-Cl-m-cr. % |
|---|---|---|---|---|
| Crude mixture | 7.10 | 0.93 | 59.50 | 32.22 |
| Product | 60.07 | 3.29 | 14.24 | 21.91 |

What is claimed is:

1. A process for hydrodehalogenating halogenated meta-cresols of formula (I)

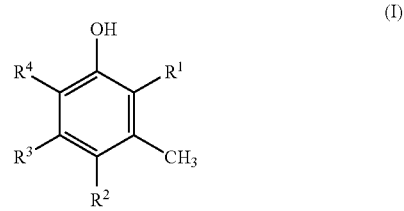

(I)

in which the $R^1$ to $R^4$ radicals are each independently hydrogen or halogen, but at least one of these radicals is halogen, comprising:
a) preparing a catalyst by applying one or more salts of palladium and/or platinum and optionally copper salts to an aluminum oxide or titanium oxide support material; and
b) contacting the halogenated meta-cresols of formula (I) with the catalyst together with hydrogen, at temperatures between 100 and 250° C.

2. The process according to claim 1, wherein at least two of the $R^1$ to $R^4$ radicals are each chlorine.

3. The process according to claim wherein the step of contacting is performed at a temperature of 150 to 250° C.

4. The process according to claim wherein from 0.5 to 50 mol of hydrogen is used per mole of halogen in the halogenated meta-cresol of formula (I).

5. The process according to claim 1, wherein the hydrogen is in the form of a mixture with an inert gas.

6. The process according to claim 1, wherein the preparation of the catalyst comprises applying $PdCl_2$, $PtCl_2$ and/or $PtCl_4$ to an aluminum oxide or titanium dioxide support material.

7. The process according to claim 6, wherein the preparation of the catalyst by applying $PdCl_2$, $PtCl_2$ and/or $PtCl_4$ to an aluminum oxide or titanium dioxide support material further comprises applying CuCl or $CuCl_2$ to the supped material.

8. The process according to claim 1, wherein the catalyst is prepared by applying a total amount of from 0.5 to 100 g of one or more salts of palladium and/or platinum and optionally copper salts to one liter of aluminum oxide or titanium oxide supped material.

9. The process according to claim 1, characterized in that step b) is performed at pressures in the range from 1 to 5 bar and in the gas phase.

10. The process according to claim 1, further comprising subsequent to steps a) and b):
c) collecting a product mixture of steps b) and aproviding the same for a subsequent chlorination reaction.

* * * * *